United States Patent [19]

Sciarra

[11] Patent Number: 5,131,399
[45] Date of Patent: Jul. 21, 1992

[54] PATIENT MONITORING APPARATUS AND METHOD

[76] Inventor: Michael J. Sciarra, 55 Cove Rd., Southhampton, N.Y. 11968

[21] Appl. No.: 563,260

[22] Filed: Aug. 6, 1990

[51] Int. Cl.⁵ .......................................... A61B 5/0205
[52] U.S. Cl. .................... 128/671; 128/721; 128/725; 128/903; 128/608
[58] Field of Search .............. 455/72; 128/671, 721, 128/722, 723, 724, 725, 670, 671, 668, 696, 903, 904

[56] References Cited

U.S. PATENT DOCUMENTS

| | | | |
|---|---|---|---|
| 1,986,353 | 1/1935 | Northrup | 336/20 |
| 3,953,848 | 4/1976 | Dillman | 128/903 |
| 4,166,264 | 8/1979 | Starr | 336/20 |
| 4,226,126 | 10/1980 | Hernden | 336/20 |
| 4,308,872 | 5/1982 | Watson | 128/725 |
| 4,356,486 | 10/1982 | Mount | 128/903 |
| 4,373,534 | 2/1983 | Watson | 128/725 |
| 4,494,553 | 1/1985 | Sciarra | 128/671 |
| 4,803,996 | 2/1989 | Peel | 128/696 |
| 4,893,347 | 1/1990 | Eastmond | 455/72 |
| 4,904,950 | 2/1990 | Brown | 128/903 |
| 4,909,260 | 3/1990 | Salem | 128/721 |
| 4,947,453 | 8/1990 | McGeehan | 455/202 |
| 4,969,210 | 11/1990 | Hansen | 455/188 |
| 5,029,235 | 7/1991 | Apostolos et al. | 455/72 |

FOREIGN PATENT DOCUMENTS 8600793 2/1986 European Pat. Off. ............ 128/671

OTHER PUBLICATIONS

*Modern Digital and Analog Communication Systems*, B. P. Lathi-p. 86, ©1989.

Primary Examiner—Kyle L. Howell
Assistant Examiner—Robert L. Nasser, Jr.
Attorney, Agent, or Firm—Fitzpatrick, Cella, Harper & Scinto

[57] ABSTRACT

A respiration transducer apparatus for monitoring respiratory movement in patients is disclosed which includes a transducer for detecting respiratory movement in the patient's body. The transducer includes a first inductor adapted to be positioned adjacent a portion of the patient's body and a second inductor adapted to be positioned adjacent the same portion of the body. The transducers are disposed in a substantially fixed geometric relation as an integrally fixed coil with the first and second inductors inductively reacting with each other and a forming a continuous transducing area.

8 Claims, 6 Drawing Sheets

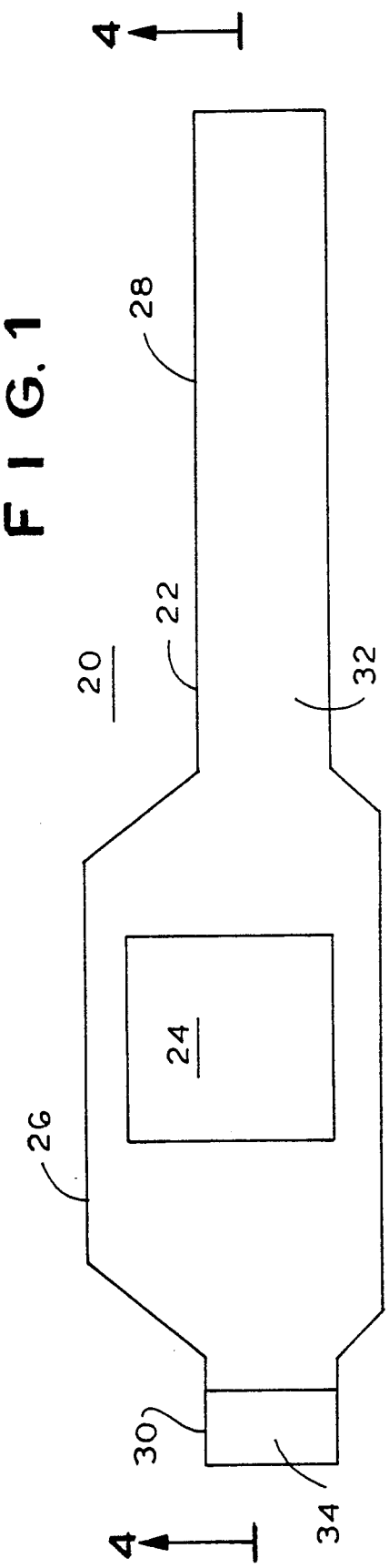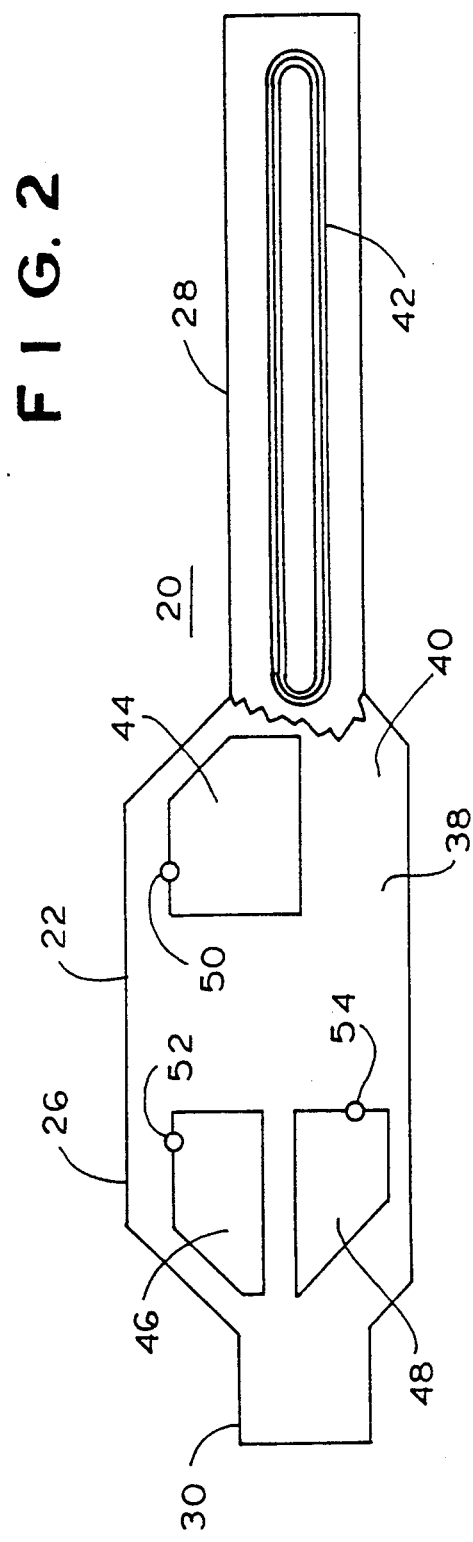

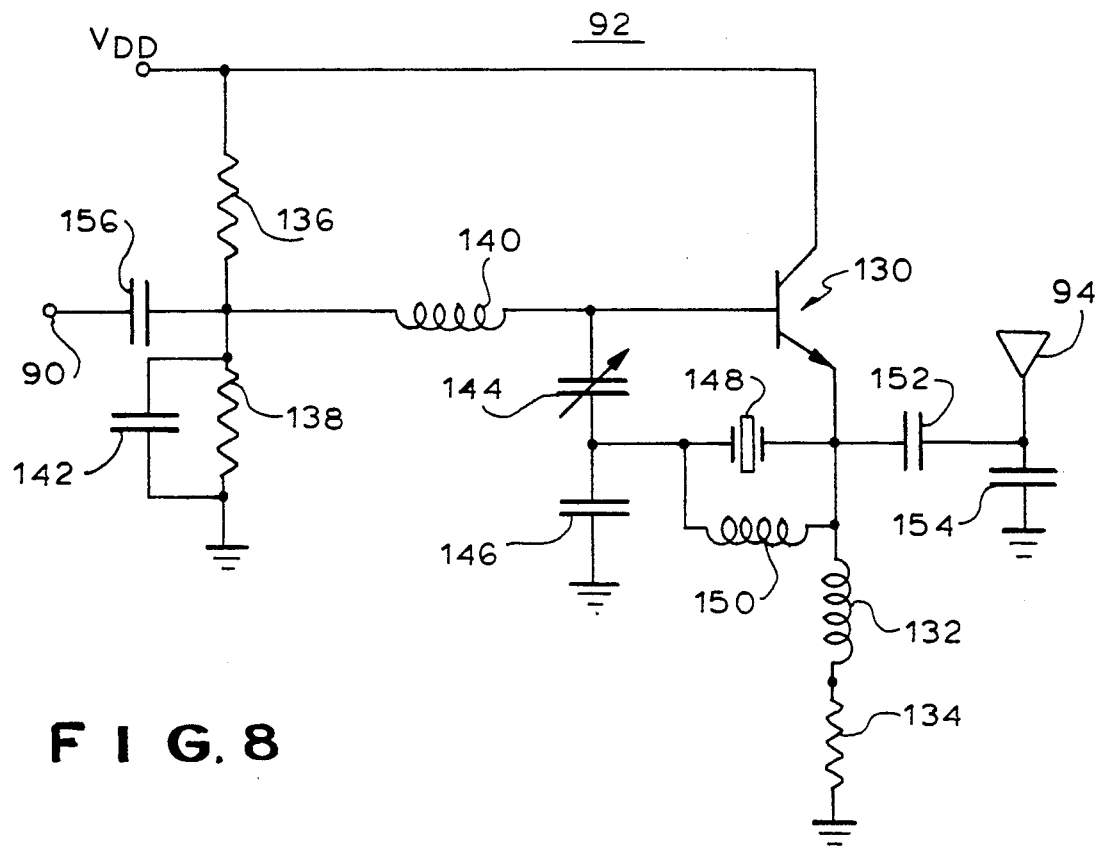
F I G. 8
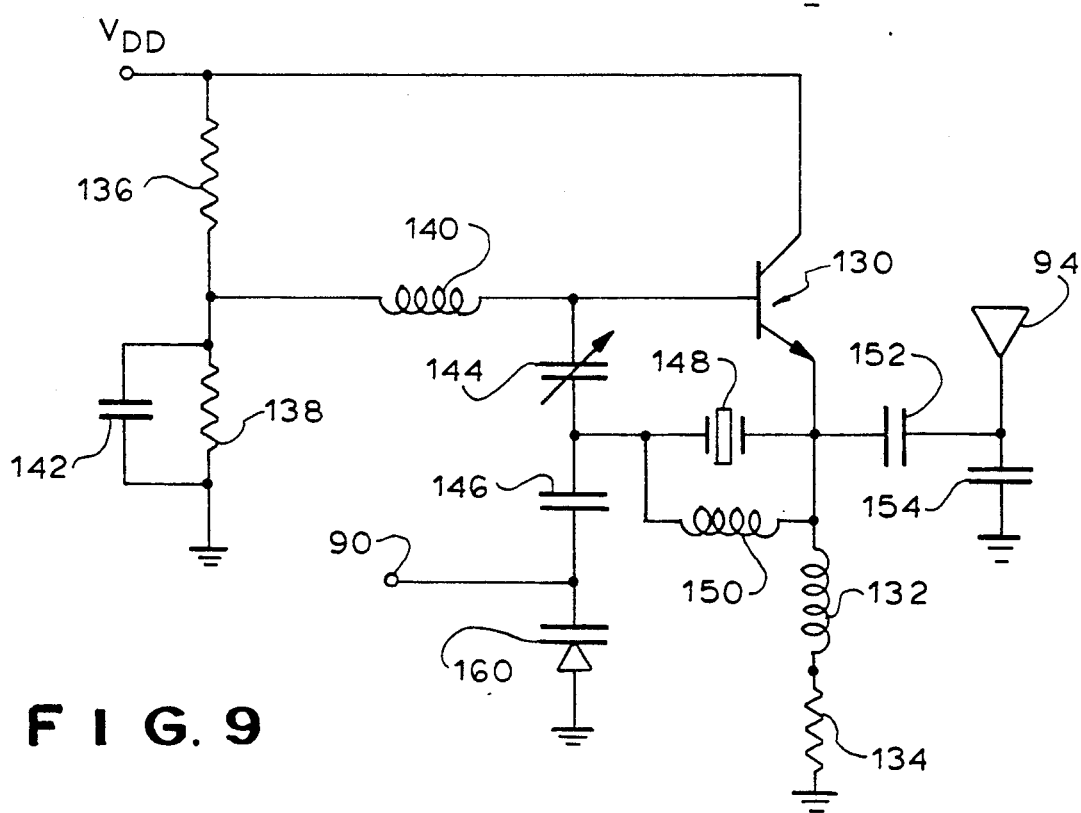
F I G. 9

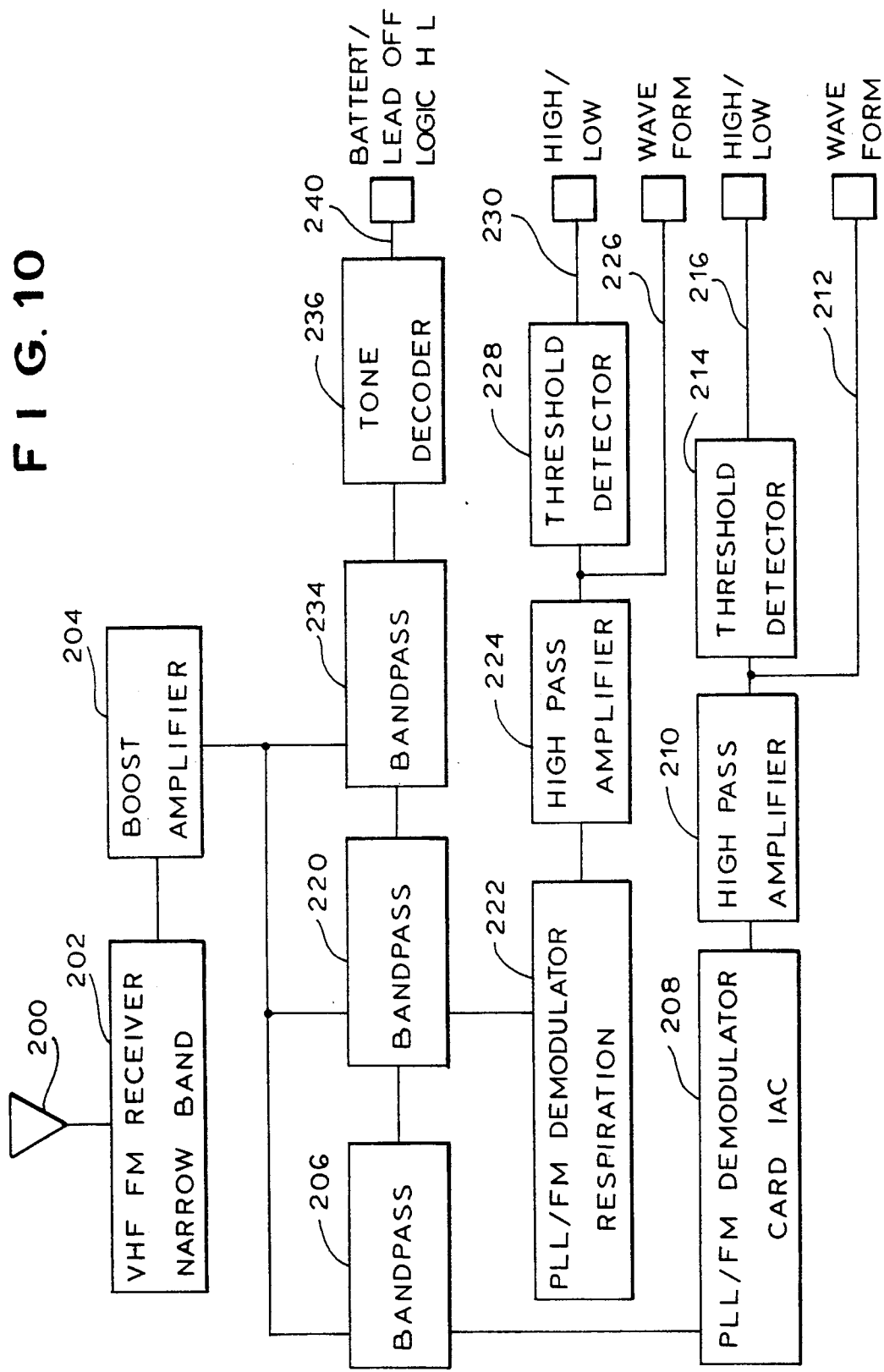

PATIENT MONITORING APPARATUS AND METHOD

BACKGROUND OF THE INVENTION

The present invention relates to the monitoring of vital signs in patients and is particularly useful for monitoring respiration in combination with other vital signs.

Apnea, the cessation of breathing or respiration, is associated with sudden infant death syndrome. Even if death does not result from an episode of apnea, irreversible brain damage may be caused. Sleep apnea is also a problem in adult patients and can have similarly severe consequences.

Accordingly, numerous attempts have been made to provide reliable and practical respiration monitors for clinical and home use. However, all such monitors have suffered from either reliability or practicality problems, or both. Consequently, the art has long felt the need to provide a patient monitor which overcomes these disadvantages.

Although it is possible to reliably monitor respiration by directly measuring air flow to and from a patient's lungs with a use of a flow meter coupled with a mask over the patient's nose and mouth, this technique is cumbersome and it is especially impractical for home use.

Since respiration monitoring of infants is often accompanied by EKG monitoring, a widely used respiration monitoring technique utilizes a measurement of thoracic impedance as it varies with the expansion and contraction of the patient's chest since this signal is easily acquired from the EKG electrodes. However, this method produces a signal having an indigenously low and highly variable signal-to-noise ratio when it is separated from the overriding EKG signal. Accordingly, the thoracic impedance signal is subject to interference by noise and the change in impedance caused by the vascular component resulting from the heart's pumping action. This problem becomes particularly troublesome when the patient's respiratory efforts diminish. Under these circumstances, signal processing circuits are prone to begin detecting the vascular component as valid respiration signals. When, for example, an infant patient's heart rate descends to between 40 and 50 beats per minute, the heartbeat's vascular component (that is, impedance change) across the patient's chest which passes through the thoracic impedance respiration filters appears identical to, and therefore intrinsically inseparable from, a valid impedance respiration waveform. Consequently, apnea can occur without being detectable by this method.

Most EKG and respiration monitors are coupled with the EKG electrodes directly by means of a cable. Although signal coupling techniques utilizing transformers or optocouplers have been adopted for reducing the potential for electric shock through the monitor itself, the mere fact that the cable provides a low resistance path to a patient's heart increases the possibility of electric shock. Further disadvantages include the possibility the patient may become entangled in the cable and the need to connect and disconnect the cable at various times.

An alternative approach to monitoring respiration utilizes a silastic strain gage containing metallic mercury which is arranged about the patient's torso and provides a variable resistance as it expands and contracts in response to changes in the size of the patient's torso with respiration. While this technique is usable in a laboratory environment, it is impractical for clinical or home use since the strain gage is relatively expensive and has a limited usable life. In addition, the strain gage must be applied to the patient's body in a state of tension which can be altered inadvertently as the patient moves. Other forms of strain gage type respiration transducers, such as piezoelectric transducers, share similar problems and are generally less sensitive and reliable. Body motion sensors have also been proposed as a means of monitoring respiration, although these devices are subject to motion artifact.

It is also possible to monitor respiration with the use of a pair of electrical inductors positioned on the torso of a patient and exhibiting a mutual inductance which varies as the patient's torso expands and contracts in the course of breathing. U.S. Pat. No. 4,494,553 to Sciarra, et al. shows a vital signs monitor which utilizes a belt positioned around a patient's chest and having a pair of coils mounted therein and spaced from each other so that, as the patient's chest moves on breathing, the coils move with respect to each other causing a change in the mutual or relative inductance of these coils. The coils are connected to a loop oscillator in a patient unit carried by the belt which forms an output signal whose frequency changes based on changes in the inductance of the coils due to the movement of the chest. Also included in the belt is a frequency modulation transmitter for transmitting respiration and cardiac signals to a nearby monitor.

However, since the inductors are spaced apart they have a relatively low mutual inductance so that breathing activity induces relatively low level changes therein. In addition, their mutual inductance is susceptible to change as a result of motion artifact. This susceptibility requires that the shape or geometry of the inductors must be fixed so that distortion of the respiration signal due to bending or other geometric distortion of the inductors is prevented. Accordingly, relatively expensive devices, such as printed circuit board inductors must be utilized. However, an optimum operating frequency range for inductive respiration monitoring is typically between about 200 and 350 kHz. This parameter, along with the fact that printed circuit board inductors permit only a limited number of turns on a single printed circuit board, require the use of multiple stacked printed circuit board inductors for monitoring respiration.

Traditional medical telemetry techniques utilize crystal controlled VHF transmitters to provide a high degree of frequency stability. However, prior art crystal controlled transmitters have required the use of high stability biasing schemes utilizing either zener diodes or voltage regulators to ensure that the transmitter will be operable. Such biasing schemes, in turn, require the use of relatively high voltages in the order of five volts or more to provide the necessary current for operating these devices. Consequently, prior art transmitters require relatively large power supplies.

Prior art medical telemetry systems also utilize either digital encoding and pulse modulation or full bandwidth analog transmission and so must operate within a relatively wide bandwidth in the order of ±20 kHz. If amplitude modulation is employed, relatively high modulation power is required, once again involving the use of a large power supply. However, if frequency modulation is instead utilized, it is difficult to carry this out with the use of a crystal controlled transmitter in the medical telemetry band of approximately 200 MHz. That is, to achieve a bandwidth of 20 kHz, it is necessary to add frequency multipliers to achieve the required deviation since crystals having a fundamental frequency of 200 MHz are not available. Moreover, frequency multiplication results in signal attenuation which requires the use of active amplification circuitry which consumes additional power. Accordingly amplitude modulation schemes typically are employed, thus requiring relatively high power and wide bandwidth operation, resulting in the possibility of signal interference from other transmissions.

The foregoing results in a large and fairly cumbersome patient unit which does not readily lend itself to a disposable-type device and the art has, therefore, employed units which are designed to be reusable. This approach is impractical of infant patient monitoring due to the relatively large size of the patient worn unit. Moreover, its clinical use for monitoring neonates is also impractical since the equipment typically becomes contaminated with body fluids and medications in this environment, thus requiring either disposability or sterilizability. Disposability is, of course, preferred since sterilization is inconvenient.

The patient unit of U.S. Pat. No. 4,494,553 aligns the cardiac transducer with the respiration transducing inductors longitudinally on the patient's thorax in order to simultaneously monitor cardiac function as well as respiration represented by the expansion and contraction of the chest cavity. Accordingly, this device is not well adapted for monitoring respiration in infants who are principally belly breathers.

It is often desirable to provide the ability to make tidal volume respiration measurements by simultaneously measuring size changes at predetermined longitudinally spaced apart positions on a patient's torso in order to detect central or obstructive apnea. This ability is not provided by the device of U.S. Pat. No. 4,494,553 which is only adapted for measuring size changes at one position. In the prior art, one tidal volume measurement device utilizes a flexible net which is arranged about the patient's entire upper torso so that the flexible net can expand and contract therewith. A pair of longitudinally spaced, single coil inductors are stitched into the net in a sawtooth configuration, so that the inductance represented by each single coil inductor varies with the expansion and contraction of the patient's torso thereunder. Each coil is coupled with a respective one of two oscillator circuits in order to vary the oscillation frequency of the corresponding circuit as the patient's torso expands and contracts. However, flexibility of the net also permits the longitudinal spacing of the inductors to change uncontrollably and undesireably.

SUMMARY OF THE INVENTION

In accordance with an aspect of the present invention, an apparatus for use in monitoring a patient's respiration comprises: disposable means for maintaining a respiration signal transducer coupled with a patient to produce a signal representing the patient's respiration; and coupling means for detachably coupling a wireless telemetry device with said disposable means for coupling the respiration transducer therewith for transmitting a respiration signal produced thereby to a wireless receiver; the disposable means including power source means for supplying operating power to the telemetry device; the coupling means including means for detachably coupling the power source means to the wireless telemetry device. Since the telemetry device, which is a relatively expensive device, is detachable, the remainder of the apparatus, which can be made relatively inexpensively, may be disposed of when it becomes contaminated with body fluids, medications or the like. Since the power source is external to the wireless telemetry device, the latter may be encased so that it may be suitably sterilized without damage.

In accordance with another aspect of the present invention, a respiration transducer comprises: a first inductor adapted to be positioned adjacent a patient; and a second inductor adapted to be positioned adjacent the patient; the first and second inductors being arranged adjacent to one another in a substantially fixed geometrical relationship. Since the inductors have a fixed geometrical relationship, they are not subject to artifact caused by relative motion therebetween, thus eliminating a potential source of respiration signal distortion. In a preferred embodiment of the present invention, the two inductors are wound together in a bifilar arrangement which is narrowly and flexibly enclosed to be positioned adjacent the patient's skin so that it moves therewith as the patient's torso expands and contracts with each breath. This preferred embodiment is especially insensitive to artifact and, due to the close coupling provided by the bifilar arrangement, a relatively strong respiration signal may be produced, as compared with an arrangement of spaced apart mutual inductors. This latter characteristic is especially advantageous for monitoring the respiration of infants.

In accordance with yet another aspect of the present invention, an apparatus for use in monitoring the medical condition of a patient comprises: a cardiac transducer; a respiration transducer; and means for maintaining said cardiac transducer on the back region of the patient and for simultaneously maintaining the respiration transducer on the abdominal region of the patient. The present invention is particularly useful for simultaneously monitoring the cardiac function of an infant patient while simultaneously monitoring the infant patient's respiration.

In accordance with still another aspect of the present invention, a transducer apparatus for performing tidal volume measurements on a patient comprises: first inductive transducing means for producing a signal representing size changes in the patient's thoracic region; second inductive transducing means for producing a signal representing size changes in the patient's abdominal region; and means for mounting the first and second inductive transducing means in a predetermined spaced relationship corresponding to a distance between transducing positions on the patient's thoracic region and abdominal region, respectively. In a preferred embodiment, each of the inductive transducing means comprises a pair of bifilar wound inductors mounted in a transducer belt so that they are appropriately spaced to position one of the inductors adjacent the patient's abdomen and the other adjacent the patient's thorax. The inductors are encased by a flexible enclosure which permits them to move with the patient's skin as it expands and contracts with respiration thus to monitor size changes in the thorax and abdomen produced thereby for reliably performing tidal volume measurements.

In accordance with a further aspect of the present invention, an apparatus for wireless transmission of a signal representing a patient's respiration comprises:

transducer means for producing a respiration signal having frequency components in a first frequency band; frequency compression means for transforming said respiration signal to a compressed respiration signal having frequency components in a second frequency band lower than the first frequency band; means for producing a transmission carrier; and modulating means for modulating the transmission carrier with the compressed respiration signal. In accordance with a related method of wireless transmission of a signal representing a patient's respiration, such method comprises the steps of: producing a respiration signal having frequency components in a first frequency band; transforming the respiration signal to a compressed respiration signal having frequency components in a second frequency band lower than the first frequency band; producing a transmission carrier; and modulating the transmission carrier with the compressed respiration signal. By modulating the carrier with a compressed respiration signal, the present invention provides the ability to transmit the respiration signal in a narrow bandwidth which is advantageous for reducing the possibility of signal interference from other sources with the use of a highly selective, narrow-band receiver.

In accordance with a still further aspect of the present invention, an apparatus for wireless transmission of an EKG signal having components in a first frequency band comprises: frequency translation means for translating the EKG signal to a frequency translated EKG signal having frequency components in a second frequency band higher than the first frequency band; means for producing a transmission carrier; and modulating means for modulating the transmission carrier with the frequency translated EKG signal. In accordance with a related method for wireless transmission of an EKG signal having components in a first frequency band, the method comprises the steps of: translating the EKG signal to a frequency translated EKG signal having frequency components in a second frequency band higher than the first frequency band; producing a transmission carrier; and modulating the transmission carrier with the frequency translated EKG signal. By modulating the transmission carrier with a frequency translated EKG signal, the apparatus and method of the present invention provides a means of preserving direct current information present in the EKG signal during wireless transmission thereof. In a preferred embodiment, the EKG signal is provided to the control terminal of a phase locked loop which is responsive thereto to produce an oscillatory signal which is frequency modulated by the amplitude of the EKG signal. The frequency modulated oscillatory signal in turn frequency modulates the transmission carrier.

In accordance with yet another aspect of the present invention, an apparatus for simultaneous wireless transmission of a first patient condition signal having frequency components in a first lower frequency band and a second patient condition signal having frequency components in a second, higher frequency band, comprises: frequency translation means for translating the first patient condition signal to a frequency translated signal having frequency components in a third frequency band higher than the first, lower frequency band of the first patient condition signal; frequency compression means for transforming the second patient condition signal to a frequency compressed signal having frequency components in a fourth frequency band lower than the second, higher frequency band; means for producing a transmission carrier; and modulating means for modulating the transmission carrier with the frequency translated signal and the frequency compressed signal. In accordance with a related method for wireless transmission of a first patient condition signal having frequency components in a first, lower frequency band and a second patient condition signal having frequency components in a second, higher frequency band, the method comprises the steps of: translating the first patient condition signal to a frequency translated signal having frequency components in a third frequency band higher than the first, lower frequency band of the first patient condition signal; transforming the second patient condition signal to a frequency compressed signal having frequency components in a fourth frequency band lower than the second, higher frequency band; producing a transmission carrier; and modulating the transmission carrier with the frequency translated signal and the frequency compressed signal. Accordingly, with the apparatus and method of the present invention, it is possible to transmit patient condition signals having widely separated frequency components in a narrow frequency band thus to permit the employment of a low power transmitter in conjunction with a sensitive and highly selective receiver which is relatively unaffected by potentially interfering signals outside of its narrow reception band.

In accordance with still another aspect of the present invention, a crystal controlled, frequency modulation VHF transmitter device comprises: a bipolar transistor; an emitter resistor coupled between the emitter of the bipolar transistor and a circuit ground; means for applying a supply voltage between the transistor's collector and the circuit ground; the supply voltage being selected between substantially one and one-half volts and three volts; high-Q feedback means for feeding back a signal from the emitter of the transistor to the base thereof to produce an oscillating signal carrier at the emitter; the high-Q feedback means including piezoelectric crystal resonator means for establishing a resonance frequency of the oscillating signal carrier; the resonance frequency being selected as an overtone frequency of the crystal resonator means; and means for frequency modulating the oscillating signal carrier. In accordance with a preferred embodiment of the present invention, a collecter-emitter bias current flowing in the transistor is selected between substantially 150 microamperes and 15 milliamperes.

The above, and other objects, features and advantages of the invention, will be apparent in the following detailed description of certain illustrative embodiments thereof which is to be read in connection with the accompanying drawings forming a part hereof, and wherein corresponding parts and components are identified by the same reference numerals in the several views of the drawings.

BRIEF DESCRIPTION OF THE DRAWINGS

FIG. 1 is a diagrammatic view of the upper surface of a combined respiration and cardiac function monitoring patient unit including a wireless telemetry device;

FIG. 2 is a diagrammatic view, partially broken away, of a lower surface of the patient unit illustrated in FIG. 1;

FIG. 8 is a schematic diagram of a first embodiment of a VHF frequency modulated crystal controlled transmitter of the wireless telemetry units of FIGS. 5 and 7;

FIG. 9 is a schematic diagram of a second embodiment of a VHF frequency modulated crystal controlled transmitter for use in the wireless telemetry units of FIGS. 5 and 7;

FIG. 10 is a block diagram of a receiver unit for receiving and demodulating signals transmitted by the wireless telemetry units of FIGS. 5 and 7.

DETAILED DESCRIPTION OF CERTAIN PREFERRED EMBODIMENTS

Figure 3:
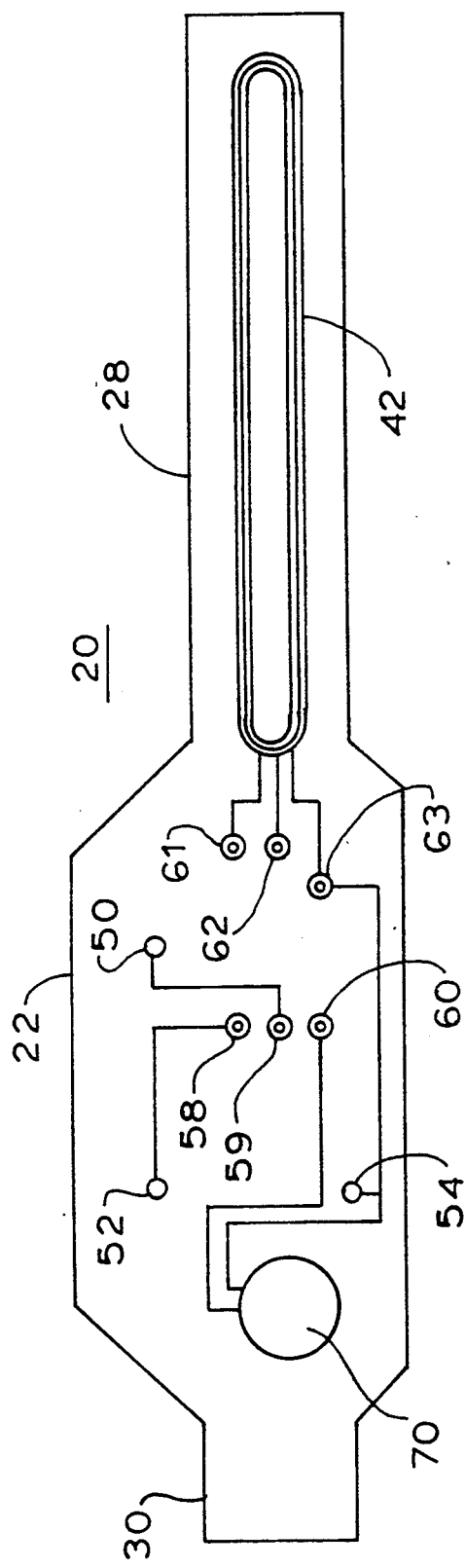
FIG. 3 is a diagrammatic view of an upper surface of the patient unit illustrated in FIG. 1 from which the wireless telemetry device and an upper cloth enclosure have been removed to illustrate certain internal elements thereof.

With reference first to FIG. 1, a patient unit 20 includes a disposable transducer belt 22 and wireless telemetry unit 24 electrically and mechanically coupled therewith in a removable fashion. The disposable transducer belt has a central portion 26, a first relatively long belt arm 28 formed integrally therewith and extending outwardly from a first side thereof, and a second, relatively shorter belt arm 30 formed integrally with the central portion 27 and extending outwardly from a second side thereof.

An upper surface 32 of the transducer belt 22 is formed of a single sheet of fabric covering the central portion 26 as well as the first and second belt arms 28 and 30. A hook and loop type fastener 34 is affixed to the upper surface 32 covering the second belt arm 30. The fastener 34 may be, for example, a hook and loop type fastener sold under the trademark "Velcro".

Figure 4:
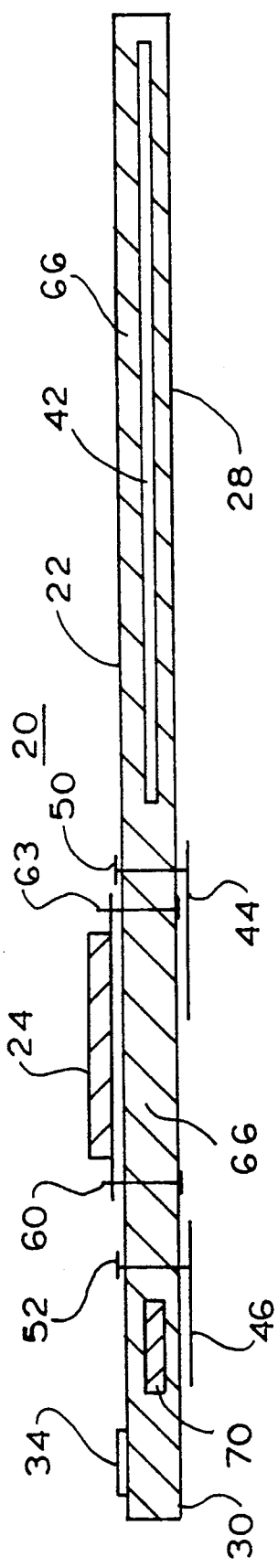
FIG. 4 is a partially sectional view of the patient unit of FIG. 1 generally along the lines 4—4 thereof.

With reference to FIG. 2, a lower surface 38 of the transducer belt 22 is therein illustrated. The lower surface is formed of a single sheet of napped fabric 40 which is shown partially cut away to expose an inductive respiration transducer 42 arranged longitudinally along the first belt arm 28. First, second and third EKG electrodes 44, 46 and 48 constructed of metal impregnated plastic are affixed to the transducer belt 22 by respective electrode rivets 50, 52 and 54 which also provide electrical connection to the respective EKG electrodes. With reference also to FIGS. 3 and 4, the inductive respiration transducer 42 includes a pair of coiled wires wound side by side to provide a relatively high mutual inductance. Preferably, the pair of coiled wires form a bifilar transformer which provides tight inductive coupling therebetween. The inductive respiration transducer 42 has a generally elongated, oval configuration so that it extends substantially along the length of the first belt arm 28.

First through sixth snap fasteners 58-63 are riveted to the central portion 26 of the transducer belt 22 and provide electrical contacts for respective terminals of the wireless telemetry unit 24. The snap fasteners 58-63 also provide a means for securely but releasably mounting the wireless telemetry unit 24 on the transducer belt 22. It will be seen from FIG. 3 that while snap fasteners 58-60 are mutually aligned, fastener 63 is offset from a line determined by the positions of fasteners 61 and 62. It will be appreciated, therefore, that the fasteners thus provide a way to ensure the correct connection of the wireless telemetry unit 24 thereto.

Respective first terminals of the two coiled wires forming the inductive respiration transducer 42 are connected together and to snap fastener 62. A second terminal of a first one of the coiled wires is connected with snap fastener 61, while a second terminal of a second one of the two coiled wires is connected with snap fastener 63. The two coiled wires are encased in a polyethylene covering so that the inductive respiration transducer 42 is relatively thin and flexible. With reference to FIG. 4, a central body 66 of the transducer belt 22 is comprised of a flexible foam layer to which the fabric sheets of the upper and lower surfaces 32 and 38 are affixed and in which the inductive respiration transducer 42 is embedded. It will be appreciated, therefore, that the first belt arm 28 is enabled to bend due to the flexible nature of both the central body 66 and the inductive respiration transducer 42.

A lithium battery 70 is embedded in the foam of the central body 66 in the central portion 26 of the transducer belt 22 and serves as a disposable power source for powering the wireless telemetry unit 24. A first terminal of the battery 70 is connected to snap fastener 60 while a second terminal thereof is connected with snap fastener 63 and thereby also to the second terminal of the second wire coil of the inductive respiration transducer 42. In order to provide electrical coupling of the EKG electrodes 44-48 with the wireless telemetry unit 24, rivets 50, 52 and 54 are electrically connected with snap fasteners 59, 58 and 63, respectively.

The patient unit 20 is especially well adapted for monitoring respiration and cardiac function in infants. In use, the lower surface 38 of the patient unit 20 is positioned adjacent the skin of an infant's torso such that the central portion 26 rests against the back of the patient's upper torso to acquire the EKG signal. At the same time, the first and second belt arms are wrapped about the anterior portion of the patient's torso so that the napped fabric of the lower surface 38 is pressed against the fastener 34 to securely yet releasably affix the patient unit about the patient.

It will be seen with reference especially to FIG. 2 that the inductive respiration transducer 42 in the first belt arm 28 is longitudinally offset with respect to the longitudinal center of the active EKG electrodes 44 and 46 (With reference to FIG. 3 of the drawings, it will be readily understood by one having ordinary skill in the art to that which the present invention pertains that electrode 48 is a reference electrode connected to the battery 70 and does not acquire the EKG signal). This offset distance is selected so that when the EKG electrodes are positioned properly against the back of the infant patient's upper torso, the first belt arm containing the inductive respiration transducer 42 is wrapped about the anterior portion of the infant's abdomen. It will be appreciated that as the infant patient breathes, its abdomen will expand and contract so that the inductive respiration transducer 42 carried by the first belt arm 28 will be geometrically distorted in correspondence with the infant patient's respiration movements so that the mutual inductance of the first and second coiled wires of the inductive respiration transducer 42 will likewise vary in correspondence with the expansion and contraction of the patient's abdomen. However, since the coils of the inductive respiration transducer 42 are wound together, so that they share a fixed geometric relationship as they are distorted by the respiratory expansion and contraction of the patient's abdomen, their mutual inductance is substantially a function of such expansion and contraction and is relatively insensitive to other motion.

Figure 5:
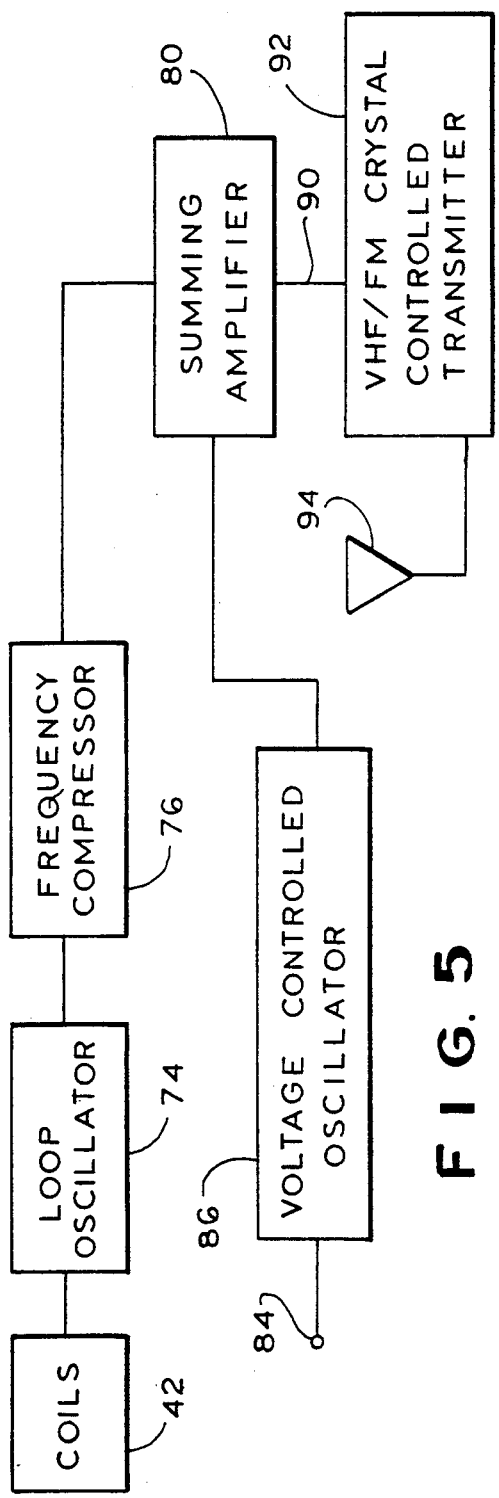
FIG. 5 is a block diagram of a wireless telemetry unit which may be used in the embodiment of FIGS. 1-4.

With reference now to FIG. 5, the coils of the inductive respiration transducer 42 are electrically coupled with a loop oscillator 74 which is tuned by the transducer 42 to oscillate at a frequency selected between 200 and 350 Khz. Loop oscillator 74 operates in a well known manner so that it produces an output signal whose frequency varies in dependance upon the mutual inductance of the coils of the inductive respiration transducer 42 within the aforementioned frequency band. An output terminal of the loop oscillator 74 is connected to an input terminal of a frequency compressor 76 which serves to frequency compress the variable frequency output signal of the loop oscillator 74 which varies in a frequency range of between 200 and 350 Khz down to a range of approximately 1,420 Hz to 1,260 Hz. The frequency compression circuit 76 in one advantageous embodiment comprises a digital counter coupled to receive the output of the loop oscillator and producing a square wave output in a frequency band of between 1,420 to 1,260 Hz, in cascade with a low pass filter which is operative to transform the square wave signal to a substantially sine wave signal. An output terminal of the frequency compressor 76 is connected to a first input terminal of a summing amplifier 80.

The EKG electrodes 44, 46 and 48 are connected with suitable EKG signal processing signal circuitry which amplifies and conditions the received EKG signals in accordance with conventional signal processing techniques and such signal processing techniques and circuitry form no part of the present invention. With reference again to FIG. 5, the amplified and conditioned EKG signals are supplied to a control input terminal 84 of a voltage controlled oscillator 86 which is operative to produce an output oscillatory signal having a frequency which varies in correspondence with the magnitude of the EKG signal and which, therefore, constitutes a signal which is frequency modulated by the EKG signal. The voltage controlled oscillator 86 produces its frequency modulated output signal to vary within a range of approximately 800 to 1,000 Hz. In one advantageous embodiment, the voltage controlled oscillator 86 is comprised of a phase locked loop which produces a frequency modulated square wave output which it supplies to a low pass filter that is operative to convert the square wave output from the phase locked loop to an essentially sine wave signal as the output of the voltage controlled oscillator 86. An output terminal of the voltage controlled oscillator 86 is connected with a second input terminal of the summing amplifier 80.

The wireless telemetry unit 24 also includes conventional circuitry for producing a "leads off" tone signifying that one or more of the EKG electrodes 44, 46 or 48 has become electrically decoupled from the patient, and is operative to produce a "low battery" tone of a different frequency in a conventional manner. These conventionally produced signals are supplied to the summing amplifier 80 through third and fourth input terminals (not shown).

The summing amplifier 80 is operative to produce a signal representing a summation of the input signals supplied to its first through fourth input terminals and supplies the summation signal to an output terminal thereof coupled with a modulation input terminal 90 of a very high frequency (VHF) frequency modulation (FM) crystal controlled transmitter 92. Transmitter 92 is operative to produce a crystal controlled carrier signal within the VHF medical telemetry band (approximately 200 MHz) which is frequency modulated by the summation signal from the summing amplifier 80 and supplied to an antenna 94 connected with an output terminal of the transmitter 92. In one advantageous embodiment, the antenna 94 is comprised of the coiled wires of the inductive respiration transducer 42.

Figure 6:
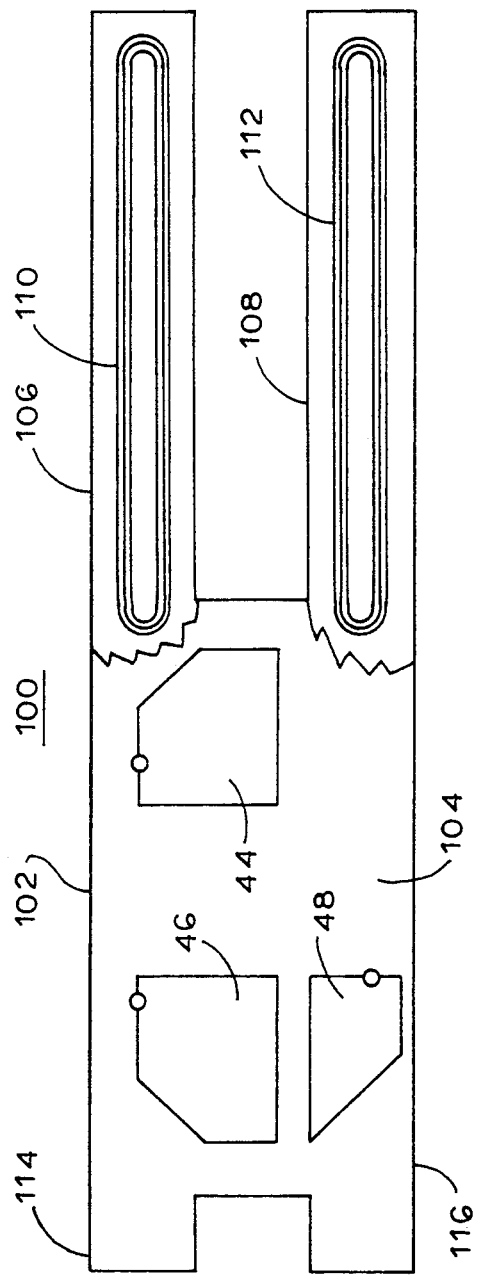
FIG. 6 is a diagrammatic view of a bottom surface of a dual respiration transducer patient unit, partially broken away.

Referring now to FIG. 6, a lower surface of a dual respiration transducer patient unit 100 is therein illustrated which is particularly useful for carrying out tidal volume measurements on infant patients. The patient unit 100 includes a transducer belt 102 having a central portion 104 and first and second elongated arms 106 and 108 formed integrally with the central portion 104 and extending from a first side thereof in longitudinally spaced relation. The lower surfaces of the elongated arms 106 and 108 are shown cut away to expose respective first and second inductive respiration transducers 110 and 112 therein. A pair of relatively shorter arms 114 and 116 are formed integrally with the central portion 104 and extend from a side thereof opposite to that from which the elongated arms 106 and 108 extend. Each of the arms 114 and 116 is aligned longitudinally with a respective one of the elongated arms 106 and 108 and includes a fastener of the same type as fastener 34 on an upper side thereof for releasably attaching each of the elongated arms to its respective arm 114 and 116, thus to securely hold the transducer belt to an infant patient. As in the case of the transducer belt 22 of FIGS. 1-4, the transducer belt 102 is positioned on the infant patient so that the electrodes 44, 46 and 48 contact the back of the patient's torso while the elongated arm 106 is wrapped about the anterior portion of the patient's chest to enable the first inductive respiration transducer 110 to produce a signal representing the expansion and contraction thereof, while the elongated arm 108 is wrapped about the anterior portion of the patient's abdomen so that the second respiration transducer 112 is positioned to produce a signal representing the expansion and contraction thereof. It will be appreciated that tidal volume measurements may thus be carried out with the use of the dual respiration transducer unit 110 illustrated in FIG. 6.

Figure 7:
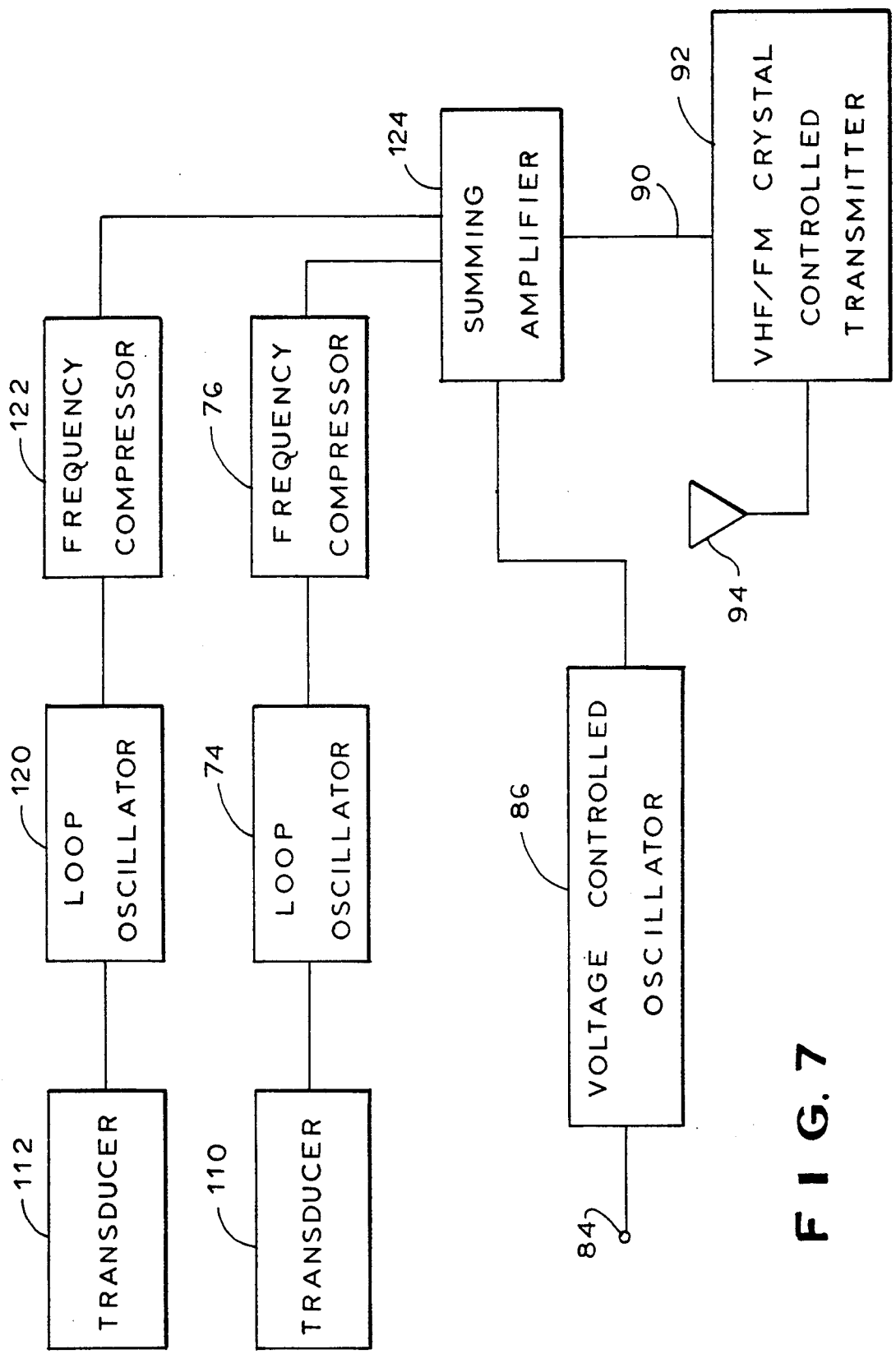
FIG. 7 is a block diagram of a wireless telemetry unit for use in the patient unit of FIG. 6.

Referring to FIG. 7, a modified wireless telemetry device suitable for transmitting the signals produced by the dual respiration transducer unit 100 is illustrated therein, in which elements corresponding to the circuit of FIG. 5 bear the same reference numerals. In FIG. 7, the inductive respiration transducer 42 has been replaced by the transducer 110, so that the frequency compressor 76 produces a frequency compressed version of a signal representing the expansion and contraction of the patient's chest. The transducer 112 is coupled with a second loop oscillator 120 operating within a frequency band distinct from that of loop oscillator 74 in order to produce a signal whose frequency varies with the expansion and contraction of the patient's abdomen as detected by the inductive respiration transducer 112. An output terminal of the loop oscillator 120 is connected with an input terminal of a second frequency compressor 122 which operates in the same fashion as the frequency compressor 76 but which produces a frequency compressed version of the signal output by the loop oscillator 120 occupying a distinct frequency band.

A summing amplifier 124 has a first input terminal connected with the output terminal of the frequency compressor 76, a second input terminal connected with the output terminal of the frequency compressor 122, a third input terminal connected with the output terminal of the voltage control oscillator 86, and fourth and fifth input terminals (not shown) for receiving the "leads off" and "low battery" signals produced in the manner described above in connection with FIG. 5. The summing amplifier 124 is operative to produce a summation signal representing a summation of the input signals received at its first through fifth input terminals. An output terminal of the summing amplifier 124 supplies the summation signal thus produced to the modulation input terminal 90 of the transmitter 92.

A first embodiment of the transmitter 92 is illustrated in FIG. 8 in the form of a modified Butler-emitter crystal controlled, low power frequency modulation transmitter circuit. The embodiment of the transmitter 92 illustrated in FIG. 8 comprises an NPN bipolar transistor 130. The collector of the transistor 130 is connected with a positive voltage terminal of the battery 70 through one of the snap fasteners 60 or 63 to receive a positive supply voltage $V_{DD}$ through a suitable precision low input-output differential voltage regulator, such as a National Semiconductor LP2951. The emitter of the transistor 130 is coupled through an RF choke 132 in series with an emitter resistor 134 to ground. The supply voltage is selected between substantially one and one-half and three volts.

A base bias voltage level is supplied by a resistive voltage divider comprised of a resistor 136 having a first terminal connected with the positive voltage source $V_{DD}$ and a second terminal connected with a first terminal of a resistor 138 whose second terminal is connected to ground. The base of the transistor 130 is coupled with the common node of the resistors 136 and 138 through an RF blocking inductor 140. Preferably, the values of the resistors 136 and 138 and of the emitter resistor 134 are selected to produce a collector-emitter current of between one hundred and fifty nanoamperes and fifteen milliamperes.

A bypass capacitor 142 is connected across the resistor 138. A variable capacitor 144 has a first terminal connected with a base of the transistor 130 and a second terminal connected with the first terminal of a fixed capacitor 146 having a second terminal connected to ground. A ninth overtone piezoelectric crystal 148 is connected between the emitter and the common node of the capacitors 144 and 146 and an inductor 150 is connected across the ninth overtone piezoelectric crystal to provide a low impedance path for signals having frequencies less than the ninth overtone frequency of the crystal 148 thus to prevent oscillation thereof below the ninth overtone frequency. The values of the capacitors 144 and 146 are selected to provide a high-Q feedback path with the crystal 148 between the emitter and base electrodes.

The emitter of the transistor 130 is coupled through a capacitor 152 to the antenna 94 and to a first terminal of a capacitor 154 having a second terminal connected to ground. In one advantageous embodiment, the antenna 94 comprises an inductive respiration transducer of the transducer belt 22 or 102 connected with the transmitter 92 through the common terminals of the two wire coils of the inductive respiration transducer.

The capacitors 152 and 154 in combination with the coils of the antenna 94 form a band pass filter tuned to the center frequency of the transmitter 92. The variable capacitor 144 is adjusted to provide maximum feedback at the transmitter's operating frequency. A capacitor 156 has a first terminal connected with the modulation input terminal 90 of the transmitter 92 and a second terminal connected with the common node of the resistors 136 and 138 to supply the modulation signal produced by the summing amplifier to the transmitter circuit 92.

With reference to FIG. 9, wherein components corresponding to those of FIG. 8 bear the same reference numerals, a second embodiment of the transmitter 92 is illustrated therein from which the capacitor 156 has been eliminated. The frequency modulation input 90 is instead connected to the second terminal of the capacitor 146 and to the cathode of a variable capacitance diode 160 whose anode is connected to ground.

With reference now to FIG. 10, a receiver unit is there illustrated in block diagram format having a receiving antenna 200 connected with the antenna input terminal of a narrow band VHF FM receiver 202 which is tuned to the center frequency of the transmitter 92 and produces a signal corresponding with a signal output by the summing amplifier 80 at an output terminal of the receiver 202. The output terminal of the receiver 202 is connected with an input terminal of a boost amplifier 204 which increases the level of the demodulated summation signal output by the receiver 202 to logic levels. An output terminal of the boost amplifier 204 is connected to an input terminal of a first band pass filter 206 which is operative to attenuate signals outside of a pass band centered at the zero offset frequency of the voltage controlled oscillator 86 of FIGS. 5 and 7 thus to form a passband for the signal output by the voltage controlled oscillator 86 of the wireless telemetry unit which has been modulated by the EKG signal. This signal is output by the band pass filter 206 to a phase locked loop (PLL) FM demodulator 208 which supplies the demodulated EKG signal at an output terminal thereof coupled with an input terminal of high pass amplifier 210 which amplifies essentially all but DC levels in order to permit high gain operation thereof. An output terminal of the high pass amplifier 210 is connected with an EKG waveform output terminal 212 of the receiver unit to supply the EKG waveform for further signal processing, if desired. The output terminal of the high pass amplifier 210 is also connected with an input terminal of a threshold detector 214 which supplies a two state signal "HIGH/LOW" at an output terminal 216 of the receiver unit to provide an indication of a heart beat event.

The output terminal of the boost amplifier 204 is also connected with an input terminal of a second band pass amplifier 220 having a pass band selected to pass the frequency compressed respiration signal produced by the frequency compressor 76 of FIG. 5 and provides the band pass filtered signal at an output terminal connected with an input terminal of a phase locked loop (PLL) FM demodulator 222 which supplies a demodulated respiration signal at an output terminal thereof. The output terminal of the demodulator 222 is connected with an input terminal of a high pass amplifier 224 similar in operation to high pass amplifier 10. An output terminal of the high pass amplifier 224 is connected with a respiration waveform output terminal 226 of the receiver unit to supply a respiration waveform thereto for further signal processing, if desired. The output terminal of high pass amplifier 224 is also connected with an input terminal of a threshold detector 228 which supplies a two state signal "HIGH/LOW" at an output terminal 230 of the receiver unit indicating individual respiration events upon a change in state thereof. It will be appreciated that similar circuitry may be provided for filtering, demodulating and threshold detecting a second respiration signal, such as that provided by the frequency compressor 122 of the FIG. 7 embodiment, wherein the pass band of the band pass filter is selected appropriately to pass only the signals produced by the frequency compressor 122.

A further band pass filter 234 serves to pass only the demodulated "low battery" and "lead-off" signals which it supplies to the input of a tone decoder 236 which in turn is operative to assume either a logic high or a low state upon the receipt of either of such signals, which it then supplies to an output terminal 240 of the receiver unit.

While a device for wireless transmission by means of a radio frequency carrier is disclosed herein, it will be appreciated that the invention may also be implemented in the form of a modulated infrared, visible light or other electromagnetic-type carrier, or else by means of ultrasound. However, radio frequency transmission is preferred because of the ability to implement the same in a device in accordance with the present invention requiring a relatively small power supply and because of the relatively low directional sensitivity provided by radio frequency transmission. It will also be appreciated that the present invention is not limited to the transmission of either or both of EKG signals and respiration signals, but may also be utilized to transmit other types of patient condition signals, such as temperature, blood gas levels, etc. Moreover, the present invention while particularly useful for monitoring infant patients, is not limited to such use but is also applicable for monitoring pediatric and adult patients.

Although specific embodiments of the invention have been described in detail herein with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. Apparatus for use in monitoring a patient's respiration, comprising
   disposable flexible substrate means, including a flexible inductive respiration signal transducer, for maintaining the flexible respiration signal transducer coupled with a patient to produce a signal representing the patient's respiration;
   a wireless telemetry device for transmitting a respiration signal to a wireless receiver; and
   manually releasable coupling means for manually detachably coupling the wireless telemetry device with said transducer for transmitting a respiration signal produced thereby whereby the telemetry device can be selectively coupled and decoupled with the transducer without damaging the coupling;
   said disposable means including a non-replaceable power source mounted within the substrate for supplying operating power to said wireless telemetry device; and
   said coupling means including means for selectively and manually detachably coupling said power source means to said wireless telemetry device.

2. A respiration transducer apparatus for monitoring respiratory movement in patients, said apparatus, comprising:
   transducer means for detecting respiratory movement in a body of such a patient, said transducer means comprising a first inductor adapted to be positioned adjacent a portion of the body of the patient, and a second inductor adapted to be positioned adjacent the same portion of the body of the patient,
   wherein said first and second inductors are disposed in a substantially fixed geometric relationship as one integrally fixed coil, and
   wherein said first and second inductors mutually inductively react with each other, and form a continuous transducing area.

3. Apparatus for use in monitoring the medical condition of a patient, comprising:
   a single flexible substrate forming a belt; said substrate having an enlarged first end portion and an elongated second end portion;
   said first end portion having a longitudinal axis extending in the long direction of the belt;
   cardiac transducer means including a plurality of active electrodes mounted in said first end portion of the belt and arranged in a predetermined position and having a longitudinal center substantially parallel with the longitudinal axis of said first end portion;
   respiration transducer means mounted in said elongated second end portion of the belt, said second end portion having a longitudinal axis parallel with and offset from the the longitudinal center of said active electrodes; and
   means for releasably securing said first end portion to said second end portion to define a belt for maintaining said cardiac transducer on the back thoracic region of the patient while simultaneously maintaining said respiration transducer on the front abdominal region of the patient.

4. A transducer apparatus for performing tidal volume measurements of a patient comprising:
   a single flexible substrate forming a belt; said substrate having an enlarged first end portion and a pair of spaced elongated and parallely extending tongues projecting from said enlarged first end portion to free ends;
   first inductive transducing means mounted in one of said tongues for producing a signal representing size changes in the patient's thoracic region;
   second inductive transducing means mounted in the other of said tongues, parallel to the first transducing means for producing a signal representing size changes in the patient's abdominal region; and
   means for releasably securing said free ends of said tongues to said first end portion to define a unitary belt thereby to position said first and second inductive transducing means in a predetermined spaced relationship corresponding to a distance between transducing positions on the patient's thoracic region and abdominal region, respectively.

5. An apparatus for use in the wireless transmission of a signal representing a patient's respiration, comprising:

inductive transducer means for producing a respiration signal having frequency components in a first frequency band;

frequency compression means for transforming said respiration signal to a compressed respiration signal having frequency component in a second relatively narrow frequency band lower than said first frequency band and for separating the frequency bands such that frequency components do not coincide in the second frequency band;

FM single stage crystal controlled means for producing a transmission carrier; and modulating means for modulating said transmission carrier with said compressed respiration signal.

6. An apparatus for use in the wireless transmission of an EKG signal having components in a first frequency band, comprising:

frequency translation means for translating said EKG signal having components in a first frequency band to a frequency translated EKG signal having frequency components in a relatively narrow second frequency band higher than said first frequency band and for separating the frequency bands such that frequency components do not coincide in the second frequency band;

FM single stage crystal controlled transmitter means for producing a transmission carrier; and modulating means for modulating said transmission carrier with said frequency translated EKG signal.

7. An apparatus for use in simultaneous wireless transmission of a first patient condition signal having frequency components in a first patient condition signal having frequency components in a first, lower frequency band, and a second patient condition signal having frequency components in a second, higher frequency band, said apparatus comprising:

frequency translation means for translating said first patient condition signal to a frequency translated signal having frequency components in a third frequency band higher than the first, lower frequency band of said first patient condition signal and for separating the frequency bands such that frequency components do not coincide;

frequency compression means for transforming said second patient condition signal to a frequency compressed signal having frequency components in a fourth frequency band lower than said second, higher frequency band and separating the frequency bands such that frequency components do not coincide;

FM single stage crystal controlled transmitter means for producing a transmission carrier; and modulating means for modulating said transmission carrier with said frequency translated signal and said frequency compressed signal.

8. Apparatus as defined in claim 4 including cardiac transducer means mounted in said first end portion of the belt and adapted to be placed over the bank thoracic region of the patient.

* * * * *